US00PP21611P2

(12) United States Plant Patent
Scrivens

(10) Patent No.: US PP21,611 P2
(45) Date of Patent: Jan. 11, 2011

(54) ROSE PLANT NAMED 'SCRIVJEAN'
(50) Latin Name: *Rosa hybrida*
Varietal Denomination: Scrivjean

(75) Inventor: Leonard William Scrivens, Kidderminster (GB)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/584,122

(22) Filed: Aug. 31, 2009

(51) Int. Cl.
*A01H 5/00* (2006.01)

(52) U.S. Cl. ..... Plt./102
(58) Field of Classification Search ..... Plt./102, Plt./141
See application file for complete search history.

*Primary Examiner*—June Hwu
(74) *Attorney, Agent, or Firm*—C. A. Whealy

(57) ABSTRACT

A new and distinct cultivar of Rose plant named 'Scrivjean', characterized by its upright, low spreading and mounding plant habit; dense and glossy foliage; freely branching growth habit; freely flowering habit; large light pink, yellow and white-colored flowers; resistance to Black Spot; and good garden performance.

2 Drawing Sheets

Botanical designation: *Rosa hybrida*.
Cultivar denomination: 'SCRIVJEAN'.

BACKGROUND OF THE INVENTION

The present Invention relates to a new and distinct cultivar of Rose plant, botanically known as *Rosa hybrida*, commercially used as an ornamental shrub, and hereinafter referred to by the name 'Scrivjean'.

The new Rose plant is a product of a planned breeding program conducted by the Inventor in Kidderminster, Worcester, United Kingdom. The objective of the breeding program was to develop new uniform Rose varieties with attractive flower coloration and better disease resistance.

The new Rose plant originated from a cross-pollination made by the Inventor in 1994 of *Rosa hybrida* 'Flower Carpet', disclosed in U.S. Plant Pat. No. 7,282, as the female, or seed, parent with *Rosa hybrida* 'Shine On', not patented, as the male, or pollen, parent. The new Rose plant was discovered and selected by the Inventor in 1995 as a single flowering plant within the progeny of the stated cross-pollination in a controlled environment in Kidderminster, Worcester, United Kingdom.

Asexual reproduction of the new Rose plant by softwood cuttings at Kidderminster, Worcester, United Kingdom since 1997, has shown that the unique features of this new Rose plant are stable and reproduced true to type in successive generations of asexual reproduction.

SUMMARY OF THE INVENTION

The following traits have been repeatedly observed and are determined to be the unique characteristics of 'Scrivjean'. These characteristics in combination distinguish 'Scrivjean' as a new and distinct cultivar of Rose:

1. Upright, low spreading and mounding plant habit.
2. Dense and glossy foliage.
3. Freely branching growth habit.
4. Freely flowering habit.
5. Large light pink, yellow and white-colored flowers.
6. Resistant to Black Spot.
7. Good garden performance.

Plants of the new Rose differ from plants of the female parent, 'Flower Carpet', in the following characteristics:

1. Plants of the new Rose are more compact than plants of 'Flower Carpet'.
2. Plants of the new Rose have darker green-colored leaves than 'Flower Carpet'.
3. Plants of the new Rose and 'Flower Carpet' differ in flower color as plants of 'Flower Carpet' have deep pink-colored flowers.

Plants of the new Rose differ from plants of the male parent, 'Shine On', in the following characteristics:

1. Plants of the new Rose are more prostrate than and not as upright as plants of 'Shine On'.
2. Plants of the new Rose and 'Shine On' differ in flower color as plants of 'Shine On' have orange and pink-colored flowers.
3. Plants of the new Rose are more resistant to Black Spot than plants of 'Shine On'.

Plants of the new Rose can be compared to plants of the *Rosa hybrida* 'Horcoherent', disclosed in U.S. Plant Pat. No. 15,982. Plants of the new Rose differ from plants of 'Horcoherent' in the following characteristics:

1. Plants of the new Rose are more freely flowering than plants of 'Horcoherent'.
2. Plants of the new Rose and 'Horcoherent' differ in flower color as plants of 'Horcoherent' have orange, pink and yellow-colored flowers.

BRIEF DESCRIPTION OF THE PHOTOGRAPHS

The accompanying colored photographs illustrate the overall appearance of the new Rose plant, showing the colors as true as it is reasonably possible to obtain in colored reproductions of this type. Colors in the photographs may differ slightly from the color values cited in the detailed botanical description which accurately describe the colors of the new Rose.

The photograph on the first sheet comprises a top perspective view of a typical plant of 'Scrivjean'.

The photograph on the second sheet is a close-up view of typical flowers, flower buds and leaves of 'Scrivjean'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown in Grand Haven, Mich., in an outdoor nursery and under commercial production practices during the spring and summer. Plants were three years old when the photographs and description were taken. In the following description, color references are made to The Royal Horticultural Society Colour Chart, 1995 Edition, except where general terms of ordinary dictionary significance are used.

Botanical classification: *Rosa hybrida* 'Scrivjean'.

Parentage:

*Female, or seed, parent.*—*Rosa hybrida* 'Flower Carpet', disclosed in U.S. Plant Pat. No. 7,282.

*Male, or pollen, parent.*—*Rosa hybrida* 'Shine On', not patented.

Propagation:

*Type.*—By softwood cuttings.

*Time to initiate roots.*—About 12 days at 25° C.

*Time to produce a rooted young plant.*—About three months at 25° C.

*Root description.*—Fine to thick; somewhat fibrous; white to brown in color.

*Rooting habit.*—Freely branching; dense.

Plant description:

*Plant form.*—Upright, low spreading and mounding perennial shrub.

*Growth habit.*—Vigorous growth habit.

*Branching habit.*—Freely basal branching habit; about 65 lateral branches per plant; dense and bushy growth habit.

*Plant height.*—About 44 cm.

*Plant width* (*spread*).—About 82 cm.

*Lateral branches.*—Length: About 16 cm. Diameter: About 3 mm. Internode length: About 2.2 cm. Strength: Strong. Texture: Smooth, glabrous. Color: Close to 146C. Thorns: None observed.

Foliage description:

*Arrangement.*—Alternate; pinnately compound.

*Leaf length.*—About 7 cm.

*Leaf width.*—About 4.5 cm.

*Leaflet length.*—About 2.2 cm.

*Leaflet width.*—About 1.7 cm.

*Leaflet shape.*—Ovate.

*Leaflet apex.*—Acute.

*Leaflet base.*—Obtuse.

*Leaflet margin.*—Serrulate.

*Leaflet texture, upper and lower surfaces.*—Smooth, glabrous.

*Leaflet luster, upper and lower surfaces.*—Glossy.

*Leaflet venation pattern.*—Pinnate.

*Leaflet color.*—Developing and fully expanded leaflets, upper surface: Close to 146A; venation, close to 146A. Developing and fully expanded leaflets, lower surface: Close to 144A; venation, close to 144A.

*Leaf petiole.*—Length: About 2 cm. Diameter: About 2 mm Texture, upper and lower surfaces: Smooth, glabrous. Color, upper and lower surfaces: Close to 144A.

Flower description:

*Flower type and habit.*—Rotate flowers arranged in terminal clusters with about three to five flowers per cluster; flowers face mostly upright.

*Natural flowering season.*—Plants flower in the landscape from June until frost in Grand Haven, Mich.; during this period flowering is continuous; flowers not persistent.

*Postproduction longevity.*—Flowers typically last about ten to twelve days on the plant.

*Fragrance.*—Slightly fragrant; typical of Rosa; sweet, pleasant.

*Flower buds.*—Height: About 2.4 cm. Diameter: About 1.1 cm. Shape: Ovoid. Color: Close to 144A.

*Flowers.*—Diameter: About 4.5 cm. Depth: About 2.2 cm.

*Petals.*—Quantity per flower: About 30 in several whorls. Length: About 2 cm. Width: About 1.2 cm. Shape: Roughly orbicular. Apex: Obtuse. Base: Attenuate. Margin: Entire. Texture, upper and lower surfaces: Smooth, glabrous; velvety. Color: Developing petals, upper surface: Initially, close to 37A becoming closer to 36A with development; towards the base, close to 6A. Developing petals, lower surface: Close to 1D. Fully expanded petals, upper surface: Towards the apex, close to 36D; mid-section, close to 155A; towards the base, close to 6A; intensity of the pink coloration is enhanced under lower temperature and/or lower light levels; with development, color becoming closer to 157D. Fully expanded petals, lower surface: Close to 157D.

*Sepals.*—Quantity per flower: Five. Length: About 1.9 cm. Width: About 4 mm. Shape: Lanceolate. Apex: Acute. Base: Fused. Margin: Entire. Texture, upper and lower surfaces: Smooth, glabrous; margin, pubescent. Color: Developing and fully expanded sepals, upper surface: Close to 144B. Developing and fully expanded, lower surface: Close to 195B.

*Peduncles.*—Length: About 2.2 cm. Diameter: About 2 mm. Orientation: Erect to about 25° from vertical. Strength: Strong. Color: Close to 144B.

*Reproductive organs.*—Stamens: Quantity per flower: Numerous, about 75. Anther shape: Oblong. Anther length: About 1 mm. Anther color: Close to 25A. Pollen amount: Moderate. Pollen color: Close to 25A. Pistils: Quantity per flower: About 25. Pistil length: About 3 mm. Stigma shape: Rounded. Stigma color: Close to 6D. Style length: About 3 mm. Style color: Close to 6D. Ovary color: Close to 144B.

*Seeds/fruits.*—Seed and fruit development has not been observed.

Pathogen/pest resistance: Plants of the new Rose have been observed to be resistant to Black Spot. Plants of the new Rose have not been observed to be resistant to pests and other pathogens common to Roses.

Garden performance: Plants of the new Rose have been observed have good garden performance and to tolerate rain, wind and temperatures ranging from about −25° C. to about 30° C.

It is claimed:

1. A new and distinct Rose plant named 'Scrivjean' as illustrated and described.

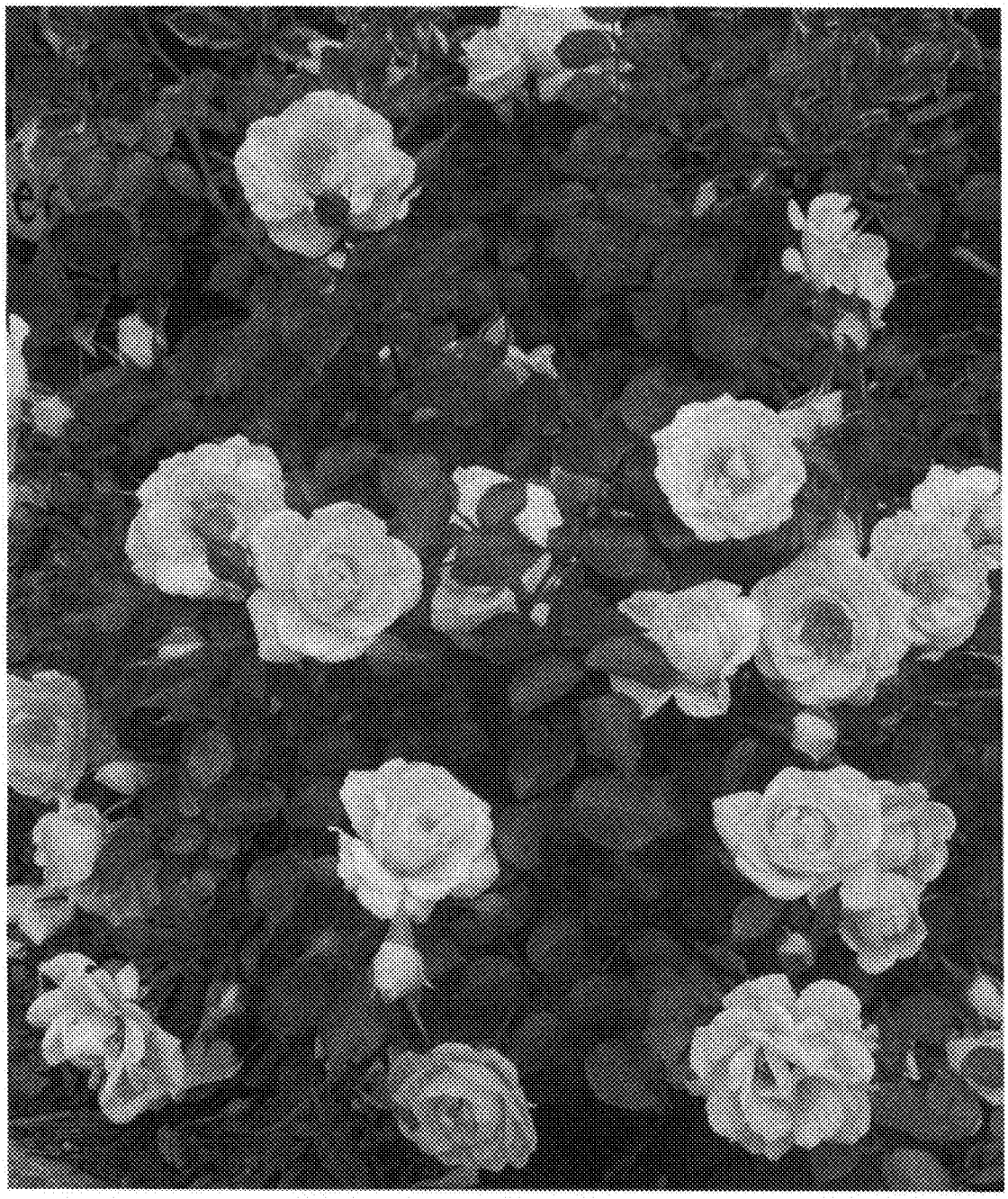

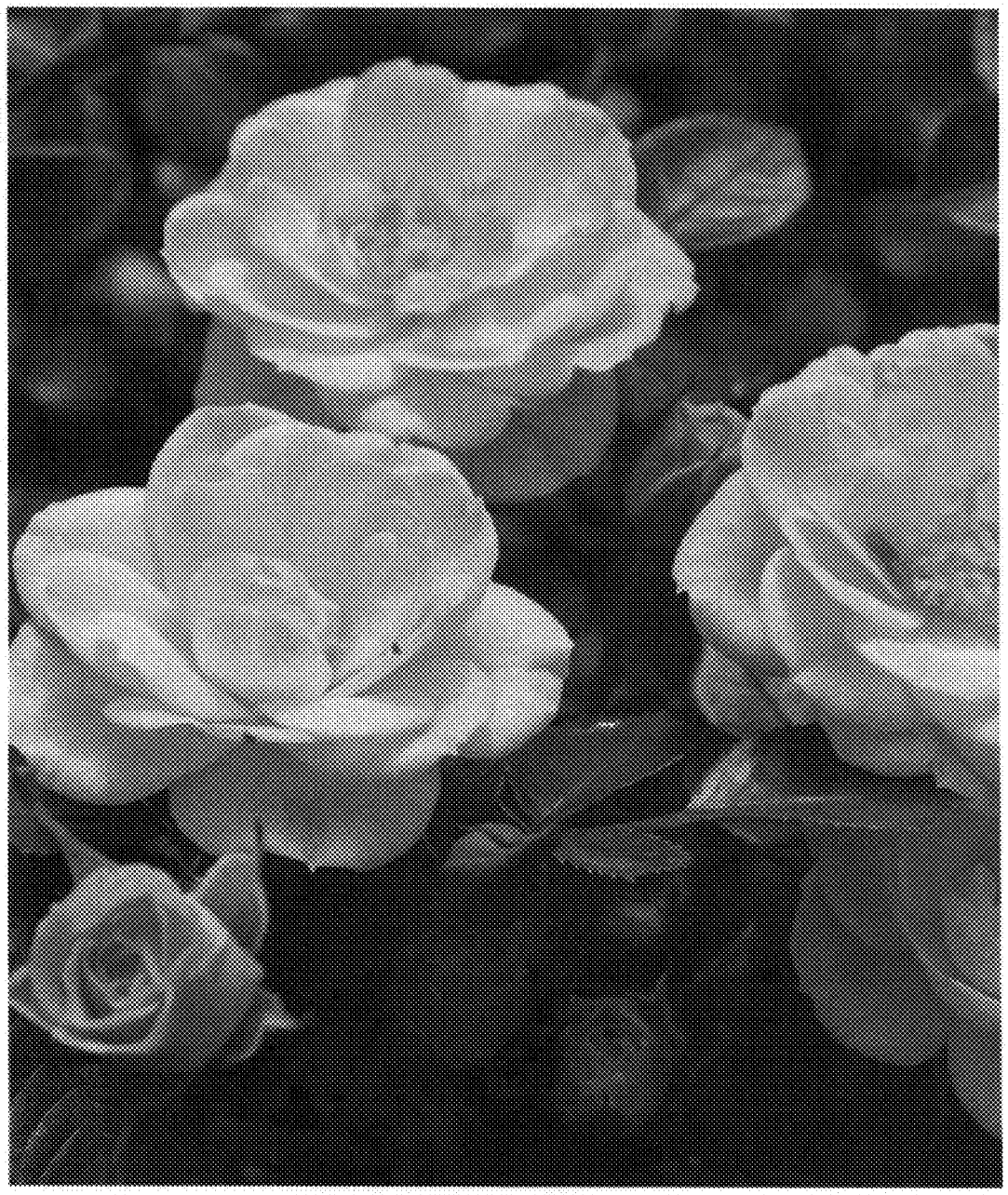

* * * * *